United States Patent [19]

Tomita et al.

[11] Patent Number: 5,296,464
[45] Date of Patent: Mar. 22, 1994

[54] BIOACTIVE AGENTS AND COMPOSITIONS FOR MATERIALS COMPRISING THE BIOACTIVE AGENT AND A METHOD FOR TREATING MATERIALS THEREWITH

[75] Inventors: Mamoru Tomita; Seiichi Shimamura, both of Yokohama; Yasuo Fukuwatari, Kawasaki; Hiroshi Miyakawa, Kamakura; Hitoshi Saito, Warabi, all of Japan

[73] Assignee: Morinaga Milk Industry Co., Ltd., Tokyo, Japan

[21] Appl. No.: 780,535

[22] Filed: Oct. 21, 1991

Related U.S. Application Data

[63] Continuation of Ser. No. 483,864, Feb. 23, 1990, abandoned.

[30] Foreign Application Priority Data

Feb. 25, 1989 [JP]  Japan .................................. 1-44273

[51] Int. Cl.$^5$ .................... A23L 3/3463; A61K 37/14; C07K 15/22; C12N 1/38
[52] U.S. Cl. ......................... 514/6; 424/439; 424/442; 426/322; 426/335; 426/532; 425/244; 530/400
[58] Field of Search .................. 530/400, 832, 873; 514/2, 6, 21; 424/439, 992; 435/252.6, 252.9, 244; 426/322, 334, 335, 442, 532

[56] References Cited

U.S. PATENT DOCUMENTS 5,240,909  8/1993  Nitsche ................................. 514/8

FOREIGN PATENT DOCUMENTS 130228  1/1985  European Pat. Off. ......... 435/252.9

OTHER PUBLICATIONS

"Iron-Binding Proteins in Milk and Resistance to *Escherichia coli* Infection in Infants" by J. J. Bullen et al, British Medical Journal, Jan. 8, 1972, pp. 69-75, 1972.
"Comparative Studies on the Chemical and Immunochemical Properties of Human Milk, Human Pancreatic Juice and Bovine Milk Lactoferrin", Chi-Sun Wang et al, Comp. Biochem. Physiol, vol. 78B, No. 3, pp. 575-580, 1984.
"Comparative Study of the Primary Structures of Sero-, Lacto- and Ovotrans-Ferrin Glycans from Different Species", by G. Spik et al, Biochimie 70 (1988), pp. 1459-1469.
"Isolation and Characterisation of Lactoferrin Separated from Human Whey by Adsorption Chromatography Using Cibacron Blue F3G-A Linked Affinity Adsorbent", Clinica Chimica Acta, 157 (1986) pp. 89-93, by W. R. Bezwoda et al.
"Milk Proteins, Chemistry and Molecular Biology", vol. II, 1971, Academic Press, Edited by Hugh A. McKenzie, Chapter 16 on Minor Milk Proteins and Enzymes, pp. 367-375.

(List continued on next page.)

Primary Examiner—Jeffrey E. Russel
Attorney, Agent, or Firm—Oblon, Spivak, McClelland, Maier & Neustadt

[57] ABSTRACT

Bioactive agents consisting of one or more lactoferrin-compounds selected from the group consisting of Zn-, Cu- and Mn-lactoferrin and having selective biological activities, i.e. growth-inhibitory activity against certain harmful microorganisms on one hand and growth-promoting activity upon certain useful microorganisms on the other hand; as well as compositions, products or materials therefor comprising the bioactive agents consisting of one or more lactoferrin-compounds selected from the group; and a method for treating materials, which are edible for human beings or animals or which are applicable to a portion of body of human beings or animals, with the bioactive agents consisting of one or more lactoferrin-compounds selected from the group consisting of Zn-, Cu- and Mn-lactoferrin or the compositions comprising the bioactive agent consisting of one or more lactoferrin-compounds selected from the group consisting of Zn-, Cu- and Mn-lactoferrin as an effective component.

18 Claims, No Drawings

OTHER PUBLICATIONS

"Zinc and Copper Binding Proteins in Human Milk", The American Journal of Clinical Nutrition 36: Dec. 1982, by Bo Lonnerdal et al, pp. 1170–1176.

"Lactofferin in Milk from Different Species", Comp. Biochem. Physiol., 1971, vol. 39B, pp. 119–129, by P. L. Masson et al., Pergamon Press/Great Britain.

Welsh et al., The Journal of Pediatrics, vol. 94 (1979), pp. 1–9.

Nonnecke et al., Journal of Dairy Science, vol. 67 (1984), pp. 606–613.

Stephens et al., Immunology, vol. 41 (1980), pp. 597–603.

Blakeborough et al., Zinc Binding in Cow's Milk and Human Milk, vol. 209, Biochem. J (1983), pp. 505–512, Great Britain.

Broxmeyer et al., Specificity and Modulation of the Action of Lactoferrin, a Negative Feedback Regulator of Myelopoiesis, Blood, vol. 55, No. 2 (1980), pp. 324–333.

Davidson et al., Fe-Saturation and Proteolysis of Human Lactoferrin: Effect on Brush-Border Receptor-Mediated Uptake of Fe and Mn, Am. J. Physiol., vol. 257 (1989), G930–4.

Lonnerdal et al., Manganese Binding Proteins in Human and Cow's Milk The American Journal of Clinical Nutrition, vol. 41 (1985), pp. 550–559, USA.

BIOACTIVE AGENTS AND COMPOSITIONS FOR MATERIALS COMPRISING THE BIOACTIVE AGENT AND A METHOD FOR TREATING MATERIALS THEREWITH

The present application is a continuation of application Ser. No. 07/483,864, filed Feb. 23, 1990, now abandoned.

FIELD OF THE INVENTION

The present invention relates to bioactive agents having biological activities and utilization of same.

More particularly, the present invention relates to bioactive agents having selective biological activities which may inhibit proliferation of harmful microorganisms and which may enhance proliferation of useful microorganisms, and utilization of same.

BACKGROUND OF THE INVENTION

Lactoferrin is known as an iron-binding protein occurring, in vivo, in lacrima, saliva, peripheral blood and milk and the like of animals inclusive of human beings. It is said that the lactoferrin content in cow's milk is 1/10 of that in human milk. It is also known that bovine lactoferrin has antibacterial activity to certain harmful microorganisms belonging to the genuses of Escherichia, Candida and Clostridium and the like [cf: Welsh, J. K. and J. T. May; Journal of Pediatrics; Vol. 94; Page 1; 1979].

It has been also reported that bovine apolactoferrin, which is obtainable by unbinding iron from lactoferrin originating from cow's milk, may inhibit proliferation of certain harmful microorganisms belonging to the genuses of Escherichia, Staphylococcus and Enterococcus and the like in synthetic culture medium with a concentration of 0.5–30 mg apolactoferrin per ml media [Nonnecke, B. J. and K. L. Smith; Journal of Dairy Science; Vol. 67; Page 606; 1984].

It has been considered in general that apolactoferrin may act to inhibit proliferation of microorganisms, which require iron strongly, due to chelation of iron with apolactoferrin in the environment thereof. A considerable quantity of apolactoferrin is needed, however, when apolactoferrin is utilized alone, to show its antibacterial activity. Consequently, there was a limitation of its usefulness.

It has been attempted to increase the antibacterial activity of apolactoferrin. For example, it is proposed to use lactoferrin together with lysozyme [Japanese Unexamined Patent Application Gazette No. 62(1987)249931]. It has been also reported that copresence of lactoferrin and secretory IgA may augment antibacterial activity [Stephens, S., J. M. Dolby, J. Montreuil and G. Spik; Immunology; Vol. 41; Page 597; 1980]. However, these prior art disclosures have defects in that they need additional effective components which are difficult to obtain in a quantity of industrial scale in a reasonable cost.

On the other hand, it has been known that human lactoferrin occurring in human milk may promote proliferation of Bifidobacteria which are typical and useful microorganisms found in the human intestine [Kodama; Nihon Shounika Gakukaihou (The Journal of Japanese Pediatric Society); Vol. 87; Page 1000; 1983]. However, it is difficult to obtain human lactoferrin in a quantity of industrial scale in a reasonable cost.

SOLUTION OF THE PROBLEMS

The inventors of the present application have thoroughly studied on lactoferrin, during which they found that biological activities of Zn-lactoferrin, Cu-lactoferrin and Mn-lactoferrin which are obtainable by chelating zinc, copper or manganese with bovine apolactoferrin are significantly higher than those of apolactoferrin and Fe-lactoferrin. This invention is based on the discovery.

PURPOSE OF THE INVENTION

It is an object of the present invention to provide bioactive agents having selective biological activities, that is, strong growth-inhibitory activity against certain harmful microorganisms on one hand and strong growth-promoting activity upon certain useful microorganisms on the other hand.

It is another object of the present invention to provide compositions comprising the bioactive agent consisting of one or more lactoferrin-compounds selected from the group consisting of Zn-, Cu- and Mn-lactoferrin as an effective component for the biological activities.

It is a further object of the present invention to provide those materials, comprising the bioactive agent as the effective component for the biological activities, which are edible for animals inclusive of human beings, or which are applicable onto a portion of animal's body inclusive of human beings' body. It should be noted that in the specification of this application the term "animal" is used to include human beings.

It is a still further object of the present invention to provide a method for treating materials, which are desirable to have biological activities, which are edible for animals, or which are applicable onto a portion of animal's body, with any of the bioactive agents and the compositions including the bioactive agent as the effective component.

The bioactive agents and the compositions in accordance with the present invention can be utilized by themselves as drugs for therapy against or prevention from certain infectious diseases; and as agents to be added to or to treat those materials which are desired to have the biological activities, or which are likely subject to deterioration or pollution due to proliferation of microorganisms. Typical materials to which the bioactive agents or the compositions containing the bioactive agent are added, or which are treated therewith are, for example, foods, feeds, cosmetics, drugs and the like.

Consequently, it is a further object of the present invention to provide those materials or products, which are edible for human beings and animals (hereinafter referred to as animals) or which are applicable to a portion of animal's body, containing the bioactive agent consisting of one or more lactoferrin-compounds selected from the group consisting of Zn-, Cu- and Mn-lactoferrin as an effective component.

SUMMARY OF THE INVENTION

The bioactive agents in accordance with the present invention consist of one or more lactoferrin-compounds selected from the group consisting of Zn-, Cu- and Mn-lactoferrin.

In accordance with the present invention, the bioactive agents can be mixed, as an effective component, with other materials, for example, other drugs, excipients or vehicles as far as they do not affect the biological activities of said agents, to prepare compositions having biological activities.

The bioactive agents and the compositions containing the bioactive agent referred in the above can be utilized by themselves as drugs for prevention or therapy against certain infectious diseases.

The bioactive agents and the composition containing the bioactive agent referred in the above can be utilized as additives for those materials which are likely subject to deterioration and/or pollution due to proliferation of microorganisms, or which are desirable to have the biological activities.

The bioactive agents and the composition of the present invention can be utilized as the drugs for treating those materials which are likely subject to deterioration and/or pollution due to proliferation of microorganisms, or which are desirable to have the biological activities.

DETAILED DESCRIPTION OF THE INVENTION

Any materials containing bovive lactoferrin can be used as the source of bovine lactoferrin, for example, bovine milk such as colostrum, transitional milk, matured milk, milk in later lactation. Also processed products of such materials and byproducts obtainable by processing such materials, for example, skim milk, cheese whey and the like can be utilized as the source of bovine lactoferrin.

Bovine lactoferrin can be isolated and purified from these materials, for example, by ion-exchange chromatography.

Apolactoferrin (iron-free lactoferrin) can be prepared from the resultant bovine lactoferrin in such a manner that the bovine lactoferrin is dissolved into and reacted with citric acid solution to remove or unbind iron from Fe-lactoferrin.

The resultant apolactoferrin can be dissolved into and reacted with aqueous solution of zinc sulfate, cupper sulfate or manganese sulfate, then resultant reaction mixture is subjected to ultrafiltration to thereby obtain Zn-lactoferrin, Cu-lactoferrin or Mn-lactoferrin respectively.

Thus obtained Zn-, Cu- and Mn-lactoferrins have biological activities and can be utilized, as it is, as bioactive agents or lactoferrin preparations which are useful: for prevention and/or therapy against certain infectious diseases; for growth-inhibition against certain harmful microorganisms; and for growth-promotion upon certain useful microorganisms.

The bioactive agents consisting of lactoferrin-compounds selected from the group consisting of Zn-, Cu- and Mn-lactoferrin can be added, in liquid, powdery or solid form as effective components having biological activities, to any other materials to prepare compositions having the biological activities. Typical materials to which the bioactive agents are added are: for example, materials, excipients or vehicles for drugs; and materials for foods, feeds or cosmetics and the like.

Certainly, the bioactive agents and the compositions containing the bioactive agents can be utilized as additives for those products which are desired to have the biological activities, which are likely subject to deterioration or pollution due to proliferation of microorganisms, which are edible for human beings and animals (hereinafter referred to as animals for simplicity), or which are applicable to a portion of animal's body. Typical products to which the bioactive agents are added are, for example, other drugs, cosmetics, foods and feeds.

It should be also noted that the bioactive agents and the compositions containing the bioactive agents referred in the above can be utilized as agents for treating those materials which are desired to have the biologial activities, which are likely subject to deterioration or pollution due to proliferation of microorganisms, which are edible for animals, or which are applicable to a portion of animal's body. Typical products to which the bioactive agents are added are, for example, other drugs, cosmetics, foods and feeds.

Now some exemplifying tests will be descibed hereunder for better understanding of the present invention.

TEST 1

Antibacterial activity against certain harmful microorganisms and growth-promoting activity upon certain useful microorganisms were evaluated for natural bovine-lactoferrin, apolactoferrin, Fe-, Zn-, Cu-and Mn-lactoferrin.

(1) PREPARATION OF SAMPLES (1-1) Preparation of Bovine Lactoferrin

Bovine lactoferrin was prepared by a conventional method disclosed in Example 2 in Japanese Unexamined Patent Application Gazette No. 63(1988)-152400 which is hereby incorporated herein as the description of the present invention.

(1-2) Preparation of Apolactoferrin

Into 2100 ml of purified water, 90 g of bovine lactoferrin obtained in the previous step (1-1) was dissolved, and 10% aqueous solution of citric acid was added thereto to adjust its pH to 2.5, then the resultant liquid was kept for 1 hour at room temperature to remove or unbind iron from Fe-lactoferrin. The resultant liquid was subjected to ultrafiltration and the retentate was freeze-dried thereby 87 g of powdery apolactoferrin was prepared.

(1-3) Preparation of Zn-lactoferrin

Into 700 ml of 0.05M phosphate buffer solution (pH: 7.6), 30 g of apolactoferrin obtained in the previous step (1-2) was dissolved, and the resultant solution was reacted with 285 ml of aqueous solution of 2.6 mM zinc sulfate containing 2.6 mM citric acid for 15 minutes at room temperature, then the resultant reaction mixture was subjected to ultarfiltration. The retentate was freezedried thereby 25 g of powdery Zn-lactoferrin was harvested.

(1-4) Preparation of Cu-lactoferrin

In the same manner as in the previous step (1-3), except that aqueous solution of 2.6 mM copper sulfate including 2.6 mM citric acid was used instead of zinc sulfate solution containing citric acid, 24 g of powdery Cu-lactoferrin was prepared.

(1-5) Preparation of Mn-lactoferrin

In the same manner as in the previous step (1-3), except that aqueous solution of 2.6 mM manganese sulfate including 2.6 mM citric acid was used instead of zinc sulfate solution containing citric acid, 24 g of powdery Mn-lactoferrin was prepared.

(1-6) Preparation of Fe-lactoferrin

Into 700 ml of purified water, 30 g of bovine lactoferrin was dissolved, the resultant solution was reacted with an aqueous solution of 2.6 mM iron sulfate for 24 hours at room temperature. The resultant reaction mixture was subjected to ultrafiltration, then the retentate was freeze-dried thereby 26 g of powdery Fe-lactoferrin was obtained.

(2) TESTED STRAINS

Following strains of harmful and useful microorganisms were used for this test.

① *Escherichia coli* (ATCC 11775)
② *Staphylococcus aureus* (ATCC 12600)
③ *Bacillus subtilis* (ATCC 6633)
④ *Psuedomonas fluorescens* (ATCC 13525)
⑤ *Clostridium perfringens* (ATCC 13124)
⑥ *Streptococcus pyogenes* (ATCC 12344)
⑦ *Bifidobacterium bifidum* (ATCC 15696)
⑧ *Bifidobacterium infantis* (ATCC 15697)
⑨ *Bifidobacterium breve* (ATCC 15700)
⑩ *Bifidobacterium longum* (ATCC 15707)
⑪ *Bifidobacterium pseudolongum* (ATCC 25526)
⑫ *Bifidobacterium animalis* (ATCC 25527)
⑬ *Lactobacillus acidophilus* (ATCC 4356)
⑭ *Lactobacillus casei* (ATCC 3425)

It should be noted that specific microbial strains deposited to the competent depository were used in the tests for eliminating troublesome jobs, for example, collection of microorganisms from a suitable source, isolation and identification of the microorganisms and cultivation of the identified bacteria and so on.

(3) METHOD (3-1) Test for *E. coli*, *S. aureus*, *B. subtilis* and *P. fluorescens*

(3-1-1) Preparation of Preincubated Bacterial Cultures

From each of the preservation slants of the concerned bacteria, a loop of the respective bacterial strain was taken out and spread onto standard agar culture medium (by Nissui Seiyaku), and aerobically cultivated for 16 hours at 35° C. Colonies grown on the culture medium were scraped by a platinum loop and suspended in the physiological saline so as to provide a predetermined turbidity of 2.0 (wavelength: 660 nm), thereby preincubated bacterial cultures for respective bacteria were prepared.

(3-1-2) Tests on Antibacterial activities

Into 100 ml of purified water, 1 g of Bactocasitone (trademark; by Difco) was dissolved, and the pH of the resultant solution was adjusted to 7.0 with 10% aqueous solution of sodium hydroxide, then sterilized at 115° C. for 15 minutes, thereby basic culture medium was prepared. A plurality of test culture media for each of lactoferrin-compounds prepared in step (1) were prepared by adding each of the lactoferrin-compounds which were filtered by the sterile membrane filter to remove the contaminated bacteria so as to make a 0.1% concentration of respective lactoferrin.

To each of the test culture media, each of the preincubated bacterial cultures prepared in step (3-1-1) was inoculated by 1% thereby test bacterial cultures were prepared. After measuring turbidities of the resultant test bacterial cultures, they were aerobically incubated for 16 hours at 35° C., then the turbidities after incubation were measured again.

A plurality of control bacterial cultures were preparared in the same manner as the test bacterial cultures, except that purified water was added instead of lactoferrin-compound solutions, and turbidities thereof were measured in the same manner as in the test bacterial cultures.

Growth-inhibition rate (hereinafter abbreviated as G-I rate) was calculated by the following formula:

$$\text{G-I rate } (\%) = 100 - (T16 - T0)/(C16 - C0) \times 100$$

wherein T16 means turbidity after 16 hours incubation of test bacterial culture, T0 means turbidity before incubation of test bacterial culture, C16 means turbidity after 16 hours incubation of control bacterial culture and C0 means turbidity before incubation of control bacterial culture.

(3-2) Test for *C. perfringens* and *S. pyogenes*

(3-2-1) Preparation of Preincubated Bacterial Cultures

Preincubated bacterial cultures of *C. perfringens* and *S. pyogenes* were prepared in the same manner as in step (3-1-1), except that GAM agar culture medium (by Nissui Seiyaku) was utilized instead of standard agar culture medium, and that anaerobic was carried out instead of aerobic incubation.

(3-2-2) Test on Antibacterial Activity

Into 100 ml of purified water, 1 g of GAM bouillon culture medium (by Nissui Seiyaku) was dissolved, the resulted solution was sterilized at 155° C. for 15 minutes, thereby basic culture medium was prepared. A plurality of test culture media, a plurality of test bacterial cultures and a plurality of control bacterial cultures were prepared in the same manner as in step (3-1-2). The resulted test bacterial cultures and control bacterial cultures were anaerobically incubated, the turbidities thereof before and after incubation were measured, and then the G-I rate was calculated in the same manner as in step (3-1-2).

(3-3) Test for *B. bifidum*, *B. infantis*, *B. breve*, *B. longum*, *B. pseudologum*, *B. animalis*, *L. acidophilus* and *L. casei*

(3-3-1) Preparation of Preincubated Bacterial Cultures

Preincubated bacterial cultures of the concerned bacteria were respectively preparared in the same manner as in step (3-2-1).

(3-3-2) Test on Growth-promoting Activity As in step (3-2-2), the turbidity was measured and the growth-promoting rate (hereinafter abbreviated as G-P rate) was calculated by following formula:

$$\text{G-P rate } (\%) = (T16 - T0)/(C16 - C0) \times 100 - 100$$

wherein T16 means turbidity after 16 hours incubation of test bacterial culture, T0 means turbidity before incubation of test bacterial culture, C16 means turbidity after 16 hours incubation of control bacterial culture and C0 means turbidity before incubation of control bacterial culture.

(4) THE TEST RESULTS

The results are shown in Table 1 and 2.

TABLE 1

GROWTH-INHIBITION EFFECT OF LACTOFERRIN-COMPOUNDS AGAINST HARMFUL BACTERIA

| strains | G-I rates (%) | | | | | |
|---|---|---|---|---|---|---|
| | lf | apo-lf | Fe-lf | Zn-lf | Cu-lf | Mn-lf |
| *E. coli* | 28 | 29 | 1 | 55 | 100 | 100 |
| *S. aureus* | 25 | 25 | 2 | 100 | 100 | 100 |
| *B. subtilis* | 23 | 27 | 4 | 100 | 100 | 100 |
| *P. fluorescens* | 29 | 30 | 3 | 100 | 100 | 100 |
| *C. perfringens* | 27 | 30 | 2 | 100 | 100 | 100 |
| *S. pyogenes* | 26 | 28 | 1 | 100 | 100 | 100 |

TABLE 2

GROWTH-PROMOTION EFFECT OF LACTOFERRIN-COMPOUNDS FOR USEFUL BACTERIA

| strains | G-P rates (%) | | | | | |
|---|---|---|---|---|---|---|
| | If | apo-If | Fe-If | Zn-If | Cu-If | Mn-If |
| B. bifidum | 35 | 38 | 40 | 50 | 53 | 55 |
| B. infantis | 38 | 40 | 42 | 51 | 55 | 54 |
| B. breve | 33 | 40 | 38 | 51 | 52 | 53 |
| B. longum | 37 | 42 | 41 | 52 | 56 | 57 |
| B. pseudolongum | 30 | 34 | 35 | 53 | 51 | 55 |
| B. animalis | 33 | 30 | 31 | 48 | 53 | 54 |
| L. acidophilus | 35 | 36 | 33 | 49 | 50 | 56 |
| L. casei | 34 | 35 | 36 | 45 | 50 | 54 |

TABLE 3

GROWTH-INHIBITORY EFFECT OF LACTOFERRIN-COMPOUNDS AGAINST HARMFUL BACTERIA

G-I rate (%)

| strains | Zn-lactoferrin (ppm) | | | | | | | Cu-lactoferrin (ppm) | | | | | | | Mn-lactoferrin (ppm) | | | | | | |
|---|---|---|---|---|---|---|---|---|---|---|---|---|---|---|---|---|---|---|---|---|---|
| | 10 | 30 | 50 | 100 | 250 | 500 | 1000 | 10 | 30 | 50 | 100 | 250 | 500 | 1000 | 10 | 30 | 50 | 100 | 250 | 500 | 1000 |
| E. coli | 2 | 20 | 22 | 38 | 42 | 51 | 55 | 4 | 37 | 51 | 89 | 100 | 100 | 100 | 3 | 36 | 50 | 90 | 100 | 100 | 100 |
| S. aureus | 3 | 29 | 38 | 66 | 87 | 100 | 100 | 5 | 33 | 54 | 85 | 100 | 100 | 100 | 4 | 35 | 52 | 84 | 100 | 100 | 100 |
| B subtilis | 1 | 28 | 41 | 77 | 100 | 100 | 100 | 9 | 42 | 86 | 100 | 100 | 100 | 100 | 8 | 40 | 88 | 100 | 100 | 100 | 100 |
| P. fluorescens | 3 | 24 | 36 | 64 | 89 | 100 | 100 | 6 | 35 | 57 | 82 | 100 | 100 | 100 | 5 | 36 | 59 | 80 | 100 | 100 | 100 |
| C. perfringens | 0 | 20 | 31 | 55 | 82 | 100 | 100 | 3 | 31 | 48 | 86 | 100 | 100 | 100 | 3 | 30 | 44 | 85 | 100 | 100 | 100 |
| S. pyogenes | 2 | 21 | 33 | 56 | 100 | 100 | 100 | 10 | 32 | 56 | 100 | 100 | 100 | 100 | 9 | 33 | 55 | 100 | 100 | 100 | 100 |

TABLE 4

GROWTH-PROMOTING EFFECT OF LACTOFERRIN-COMPOUNDS UPON USEFUL BACTERIA

G-P rate (%)

| strains | Zn-lactoferrin (ppm) | | | | | | | Cu-lactoferrin (ppm) | | | | | | | Mn-lactoferrin (ppm) | | | | | | |
|---|---|---|---|---|---|---|---|---|---|---|---|---|---|---|---|---|---|---|---|---|---|
| | 10 | 30 | 50 | 100 | 250 | 500 | 1000 | 10 | 30 | 50 | 100 | 250 | 500 | 1000 | 10 | 30 | 50 | 100 | 250 | 500 | 1000 |
| B. bifidum | 0 | 11 | 22 | 48 | 51 | 53 | 50 | 1 | 10 | 25 | 53 | 55 | 55 | 53 | 3 | 12 | 30 | 54 | 58 | 58 | 55 |
| B. infantis | 5 | 13 | 29 | 52 | 52 | 55 | 51 | 1 | 9 | 27 | 55 | 57 | 57 | 55 | 4 | 11 | 33 | 55 | 59 | 59 | 54 |
| B. breve | 4 | 10 | 28 | 50 | 54 | 56 | 51 | 3 | 12 | 26 | 54 | 56 | 56 | 52 | 4 | 15 | 32 | 56 | 57 | 57 | 53 |
| B. longum | 4 | 16 | 27 | 56 | 56 | 57 | 52 | 2 | 15 | 29 | 57 | 58 | 58 | 56 | 3 | 18 | 34 | 52 | 59 | 59 | 57 |
| B. pseudolongum | 3 | 15 | 25 | 51 | 53 | 55 | 53 | 1 | 14 | 27 | 50 | 55 | 55 | 51 | 2 | 13 | 29 | 51 | 56 | 56 | 55 |
| B. animalis | 3 | 15 | 26 | 47 | 50 | 51 | 48 | 2 | 13 | 28 | 55 | 55 | 55 | 53 | 2 | 14 | 28 | 53 | 56 | 56 | 54 |
| L. acidophilus | 3 | 14 | 27 | 49 | 50 | 52 | 49 | 0 | 13 | 28 | 52 | 54 | 54 | 50 | 1 | 11 | 30 | 55 | 57 | 58 | 56 |
| L. casei | 2 | 10 | 24 | 40 | 47 | 50 | 45 | 1 | 11 | 26 | 51 | 53 | 53 | 50 | 1 | 15 | 31 | 55 | 56 | 57 | 54 |

From Table 1, it will be understood that Zn-, Cu- and Mn-lactoferrin have remarkably stronger growth-inhibitory activities against all of 6 strains of harmful bacteria than other lactoferrin-compounds.

It will be also understood from Table 2 that Zn-, Cu- and Mn-lactoferrin have stronger growth-promoting activities to all of 8 strains of useful bacteria than other lactoferrin-compounds.

Test 2

This test was conducted to determine effective concentration of Zn-, Cu- and Mn-lactoferrins for selective biological activities.

(1) PREPARATION OF MATERIALS (1-1) Preparation of Zn-lactoferrin

In the same manner as in step (1-3) of Test 1, Zn-lactoferrin was prepared.

(1-2) Preparation of Cu-lactoferrin

In the same manner as in step (1-4) of Test 1, Cu-lactoferrin was prepared.

(1-3) Preparation of Mn-lactoferrin

In the same manner as in step (1-5) of Test 1, Mn-lactoferrin was prepared.

(2) TESTED STRAINS

The same bacterial strains in Test 1 were used.

(3) METHOD

The method was the same as in step (3-1-2), (3-2-2) and (3-3-2) of Test 1, except that Zn-, Cu- and Mn-lactoferrins were respectively used in various concentrations as shown in Tables 3 and 4. The rates of growth-inhibition and growth-promotion were calculated in the same manner as in Test 1.

(4) Results

The results are shown in Tables 3 and 4.

From Table 3, it will be understood that all of Zn-, Cu- and Mn-lactoferrin have growth-inhibitory activity against all of 6 strains of harmful bacteria in a concentration more than 30 ppm inclusive, that the activity is proportional to the concentration, and that the G-I rate thereof in the concentration over 250 ppm inclusive are 100% except the case of Zn-lactoferrin. In the case of Zn-lactoferrin, however, the G-I rate at 250 ppm was 42% for E. coli, and 82–100% for S. aureus, B. subtilis, P. florescens, C. perfringens and S.pyogenes.

It will be also understood from Table 4 that all of Zn-, Cu- and Mn-lactoferrin have growth-promoting activity to all of 8 strains of useful bacteria, that the activity is proportional to the concentration, and that the maximum G-P rate are resulted in the concentration between 250–500 ppm, both inclusive.

Additional tests were conducted for test samples of Zn-, Cu- and Mn-lactoferrin in which one or both of bovine lactoferrin and apolactoferrin are included, and similar results were obtained.

Now some examples will be described hereunder for better understanding of the present invention.

EXAMPLE 1

To 10 kg of raw milk, 2 g of powdery Zn-lactoferrin prepared in the same manner in step (1-3) of Test 1 was dissolved (the concentration of Zn-lactoferrin in the raw milk: 200 ppm) to thereby obtain test samples. The same quantity of raw milk to which Zn-lactoferrin was not added was prepared as control samples. The test and control samples were aseptically bottled and sealed.

The resultant samples were kept for 8 days at 10° C. to observe the change of viable bacterial counts and flavour thereof.

The results are shown in Table 5.

TABLE 5

EFFECT OF Zn-LACTOFERRIN ON PRESERVABILITY OF RAW MILK

| storage period (day) | control sample bacterial count | flavour | test sample bacterial count | flavour |
|---|---|---|---|---|
| 0 | $20 \times 10^4$ | good | $20 \times 10^4$ | good |
| 2 | $98 \times 10^4$ | good | $31 \times 10^4$ | good |
| 4 | $45 \times 10^5$ | slightly sour | $66 \times 10^4$ | good |
| 6 | $55 \times 10^6$ | putrid | $16 \times 10^5$ | good |
| 8 | $86 \times 10^7$ | putrid | $79 \times 10^5$ | slightly sour |

From Table 5, it is apparent that addition of Zn-lactoferrin to raw milk improves preservability.

EXAMPLE 2

To 800 g of skim milk powder, 200 g of powdery Zn-lactoferrin prepared in the same manner in step (1-3) of Test 1 was added to thereby obtain 1000 g of easily fluidal powdery composition having biological activities.

The resultant composition was fed to 5 healthy Holstein cows twice a day for 2 days by 30 g at a time together with ordinary feed in the morning and in the afternoon.

Viable bacterial counts in the feces before and after ingestion of Zn-lactoferrin were compared. The results are shown in Table 6.

TABLE 6

EFFECT OF DOSAGE OF Zn-LACTOFERRIN ON VIABLE BACTERIAL COUNTS IN FECES

| cow No. | E. coli before | after | C. perfringes before | after | Bifidobacterium before | after |
|---|---|---|---|---|---|---|
| 1 | $7.3 \times 10^7$ | $1.1 \times 10^7$ | $4.3 \times 10^7$ | $2.1 \times 10^6$ | $5.1 \times 10^7$ | $1.5 \times 10^8$ |
| 2 | $6.0 \times 10^8$ | $2.2 \times 10^7$ | $5.2 \times 10^7$ | $1.0 \times 10^7$ | $4.3 \times 10^7$ | $2.0 \times 10^8$ |
| 3 | $2.7 \times 10^8$ | $7.6 \times 10^7$ | $3.5 \times 10^7$ | $8.4 \times 10^6$ | $2.2 \times 10^7$ | $1.8 \times 10^8$ |
| 4 | $8.1 \times 10^7$ | $4.3 \times 10^7$ | $7.6 \times 10^6$ | $1.9 \times 10^6$ | $6.3 \times 10^7$ | $3.1 \times 10^8$ |
| 5 | $7.7 \times 10^8$ | $3.7 \times 10^8$ | $8.0 \times 10^6$ | $6.5 \times 10^5$ | $3.9 \times 10^7$ | $1.6 \times 10^8$ |

The same composition was fed to 6 young swine having diarrhea for 3 days by 10 g/day. As control swine, skim milk powder to which Zn-lactoferrin was not added was fed to 4 young swine.

Symptom of diarrhea on the swine was observed for 3 days. The results are shown in Table 7.

TABLE 7

EFFECT OF DOSAGE OF Zn-LACTOFERRIN ON DIARRHEA OF SWINE

| dose | curing rate (%) |
|---|---|
| control (skim milk powder) | 0/4 (0%) |
| composition (Zn-lf) | 4/6 (66.7%) |

From Table 6, it will be understood that viable counts of harmful bacteria in the intestine were reduced, and that those of useful Bifidobacteria were increased by dosage of the composition containing Zn-lactoferrin.

It will be also understood from Table 7 that diarrhea in swine can be cured by dosage of the composition containing Zn-lactoferrin.

EXAMPLE 3

To the mixture of 485 g of sodium acetate unhydrated and 485 g of sodium chloride, 30 g of powdery Zn-lactoferrin prepared in the same manner as in step (1-3) of Test 1 was added to thereby obtain 1000 g of an easily fluidal powdery composition.

To 4950 g of city water, 50 g of the resultant powdery composition was dissolved (concentration of the components; Zn-lf: 300 ppm; sodium acetate unhydrated: 0.485%; sodium chloride: 0.485%). In the resultant solution, 1 kg of sliced cabbage in the market was dipped for 10 minutes, then dipped out and separated and sealed into a plurality of containers. The resultant packages were kept at 8° C. for 1 week (test samples). Control samples were prepared in the same manner as in the test samples, except that Zn-lactoferrin was not included in the solution.

The appearance and taste of the treated sliced cabbage were observed for 1 week. The results are shown in Table 8.

TABLE 8

EEFECT OF Zn-LF ON PRESERVABILITY OF SLICED CABBAGE

| storage period (day) | appearance and taste of sliced cabbage control sample | test sample |
|---|---|---|
| 0 | good in appearance and taste | good in appearance and taste |
| 3 | slightly drooped, good taste | good in appearance and taste |
| 5 | browny appearance, putrid smell | slightly drooped, good taste |
| 7 | — | browny appearance, putrid smell |

From Table 8, it will be understood that preservability of sliced cabbage is improved by the treatment with aqueous solution of the composition containing Zn-lactoferrin.

To 490 g of city water, 10 g of the same composition was dissolved (concentrations of the components; Zn-lf: 600 ppm; sodium acetate unhydrated: 0.97%1 sodium chloride: 0.97%).

With the resulting solution, the breasts of a Holstein cow (of 3 years age) having mammitis were thoroughly washed or rinsed before and after milking in the morning and in the afternoon for 3 consecutive days. Mammitis was completely cured after 3 days. From the microbial inspection, mammitis was caused by S. pyogenes.

From the result of this additional test, treatment with the composition containing the Zn-lactoferrin is effective for prevention or therapy against mammitis in cow's.

EXAMPLE 4

To 10 kg of raw milk, 1 g of Cu-lactoferrin prepared in the same manner as in step (1-4) of Test 1 was dissolved (concentration of Cu-lactoferrin in the solution was 100 ppm). The resultant milk was aseptically distributed into a plurality of bottles and sealed to make test samples. Control samples were prepared in the same manner as in the test samples, except that Cu-lactoferrin was not added.

The test and control samples were preserved at 10° C. for 8 days to observe the change of viable bacterial count and flavour. The results are shown in Table 9.

TABLE 9

EFFECTS OF Cu-LF ON PRESERVABILITY OF RAW MILK

| storage period (day) | control sample bacterial count | flavour | test sample bacterial count | flavour |
|---|---|---|---|---|
| 0 | $20 \times 10^4$ | good | $21 \times 10^4$ | good |
| 2 | $95 \times 10^4$ | good | $30 \times 10^4$ | good |
| 4 | $93 \times 10^5$ | slightly sour | $63 \times 10^4$ | good |
| 6 | $68 \times 10^6$ | putrid | $10 \times 10^5$ | good |
| 8 | $95 \times 10^7$ | putrid | $57 \times 10^5$ | slightly sour |

From Table 5, it will be apparent that addition of Cu-lactoferrin improves preservability of raw milk.

EXAMPLE 5

To 800 g of skim milk powder, 200 g of powdery Cu-lactoferrin prepared in the same manner as in step (1-4) of Test 1 was added to thereby obtain 1000 g of an easily fluidal bioactive composition.

To 5 healthy Holstein cows of 2 years age, the resultant composition was fed twice a day for 2 days by 30 g at a time together with ordinary feed in the morning and in the afternoon.

Viable bacterial counts in the feces before and after ingestion of Cu-lactoferrin were compared. The results are shown in Table 10.

TABLE 10

EFFECT OF DOSAGE OF Cu-LACTOFERRIN ON VIABLE BACTERIA IN FECES

| cow No. | E. coli before | E. coli after | C. perfringes before | C. perfringes after | Bifidobacterium before | Bifidobacterium after |
|---|---|---|---|---|---|---|
| 1 | $5.6 \times 10^8$ | $2.0 \times 10^8$ | $8.7 \times 10^6$ | $2.9 \times 10^6$ | $5.9 \times 10^7$ | $7.7 \times 10^8$ |
| 2 | $4.3 \times 10^7$ | $7.7 \times 10^6$ | $6.5 \times 10^7$ | $1.1 \times 10^6$ | $6.2 \times 10^7$ | $9.1 \times 10^8$ |
| 3 | $9.2 \times 10^8$ | $1.3 \times 10^8$ | $7.2 \times 10^7$ | $8.4 \times 10^6$ | $7.5 \times 10^7$ | $8.8 \times 10^8$ |
| 4 | $3.7 \times 10^8$ | $5.8 \times 10^7$ | $3.9 \times 10^7$ | $5.9 \times 10^6$ | $5.1 \times 10^7$ | $7.4 \times 10^8$ |
| 5 | $7.7 \times 10^7$ | $2.9 \times 10^7$ | $4.3 \times 10^7$ | $5.6 \times 10^6$ | $4.3 \times 10^7$ | $6.9 \times 10^8$ |

The same composition was fed to 6 young swine having diarrhea for 3 days by 10 g/day. As control swine, skim milk powder to which Zn-lactoferrin was not added was fed to 4 young swine.

Symptom of diarrhea on the swine was observed for 3 days. The results are shown in Table 11.

TABLE 11

EFFECT OF DOSAGE OF Cu-LACTOFERRIN ON DIARRHEA OF YOUNG SWINE

| dose | curing rate (%) |
|---|---|
| control (skim milk powder) | 0/4 (0%) |
| composition (Cu-lf) | 5/6 (83.3%) |

From Table 10, it will be understood that viable counts of harmful bacteria in the intestine were reduced, and that those of useful bifidobacteria were increased by dosage of the composition containing Cu-lactoferrin. It will be also understood from Table 11 that diarrhea on swine can be cured by dosage of the composition containing Cu-lactoferrin.

EXAMPLE 6

To a mixture of 490 g of sodium acetate unhydrated and 490 g of sodium chloride, 20 g of Cu-lactoferrin prepared in the same manner as in step (1-4) of Test 1 was added to thereby obtain 1000 g of an easily fluidal powdery composition.

To 4950 g of city water, 50 g of the resultant powdery composition was dissolved (concentration of the components; Cu-lactoferrin: 200 ppm; sodium acetate unhydrated: 0.49%; sodium chloride: 0.49%). In the resultant solution, 1 kg of sliced cabbage in the market was dipped for 10 minutes, then dipped out and packed and sealed in a plurality of containers (test samples). The resultant packages were kept at 10° C. for 1 week. Control samples were prepared in the same manner as in the test samples, except that Cu-lactoferrin was not included in the solution.

The appearance and flavour of the treated sliced cabbage were observed for 1 week. The results are shown in Table 12.

TABLE 12

EEFECT OF Cu-LF ON PRESERVABILITY OF SLICED CABBAGE

| storage period (day) | appearance and taste of sliced cabbage control sample | test sample |
|---|---|---|
| 0 | good in appearance and taste | good in appearance and taste |
| 3 | slightly drooped, good taste | good in appearance and taste |
| 5 | browny appearance, putrid smell | slightly drooped, good taste |
| 7 | — | browny appearance, putrid smell |

From Table 12, it will be understood that preservability of sliced cabbage is improved by the treatment with aqueous solution of the composition containing Cu-lactoferrin.

To 490 g of city water, 10 g of the same composition was dissolved (concentrations of the components; Cu-lactoferrin: 400 ppm; sodium acetate unhydrated: 0.98%; sodium chloride: 0.98%).

With the resulting solution, the breasts of a Holstein cow (of 3 years age) having mammitis were thoroughly washed or rinsed before and after milking in the morning and in the afternoon for 3 consecutive days. Mammitis was completely cured after 3 days. From the microbial inspection, mammitis was caused by S. pyogenes.

EXAMPLE 7

To 10 kg of raw milk, 1 g of Mn-lactoferrin prepared in the same manner as in step (1-5) of Test 1 was dissolved (concentration of Mn-lactoferrin in the solution was 100 ppm). The resultant milk was aseptically distributed into a plurality of bottles and sealed to make test samples. Control samples were prepared in the same manner as in the test samples, except that Mn-lactoferrin was not added.

The test and control samples were preserved at 10° C. for 8 days to observe the change of viable bacterial count and flavour. The results are shown in Table 13.

TABLE 13

EFFECTS OF Mn-LF ON PRESERVABILITY OF RAW MILK

| storage period (day) | control sample bacterial count | flavour | test sample bacterial count | flavour |
|---|---|---|---|---|
| 0 | $20 \times 10^4$ | good | $20 \times 10^4$ | good |
| 2 | $95 \times 10^4$ | good | $28 \times 10^4$ | good |

TABLE 13-continued

EFFECTS OF Mn-LF ON PRESERVABILITY OF RAW MILK

| storage period (day) | control sample | | test sample | |
|---|---|---|---|---|
| | bacterial count | flavour | bacterial count | flavour |
| 4 | $90 \times 10^5$ | slightly sour | $60 \times 10^4$ | good |
| 6 | $77 \times 10^6$ | putrid | $12 \times 10^5$ | good |
| 8 | $99 \times 10^7$ | putird | $45 \times 10^5$ | slightly sour |

From Table 13, it will be apparent that addition of Mn-lactoferrin improves preservability of raw milk.

EXAMPLE 8

To 800 g of skim milk powder, 200 g of powdery Mn-lactoferrin prepared in the same manner in step (1–5) of Test 1 was added to thereby obtain 1000 g of an easily fluidal powdery composition having biological activities.

The resultant composition was fed to 5 healthy Holstein cows of 1–2 years age, twice a day for 2 days by 30 g at a time together with ordinary feed in the morning and in the afternoon.

Viable bacterial counts in the feces before and after ingestion of Mn-lactoferrin were compared. The results are shown in Table 14.

TABLE 14

EFFECT OF DOSAGE OF Mn-LACTOFERRIN ON VIABLE BACTERIAL COUNTS IN FECES

| cow No. | E. coli | | C. perfringes | | Bifidobacterium | |
|---|---|---|---|---|---|---|
| | before | after | before | after | before | after |
| 1 | $4.6 \times 10^8$ | $1.1 \times 10^8$ | $7.6 \times 10^6$ | $2.3 \times 10^6$ | $4.3 \times 10^7$ | $4.1 \times 10^8$ |
| 2 | $4.2 \times 10^7$ | $7.0 \times 10^6$ | $5.4 \times 10^7$ | $1.0 \times 10^7$ | $2.5 \times 10^7$ | $2.8 \times 10^8$ |
| 3 | $7.5 \times 10^8$ | $1.0 \times 10^8$ | $7.0 \times 10^7$ | $4.9 \times 10^6$ | $3.9 \times 10^7$ | $7.3 \times 10^8$ |
| 4 | $3.3 \times 10^8$ | $5.1 \times 10^7$ | $4.2 \times 10^7$ | $5.1 \times 10^6$ | $7.2 \times 10^7$ | $7.7 \times 10^8$ |
| 5 | $6.9 \times 10^7$ | $2.8 \times 10^7$ | $1.9 \times 10^7$ | $3.7 \times 10^6$ | $6.9 \times 10^7$ | $9.2 \times 10^8$ |

The same composition was fed to 6 young swine having diarrhea for 3 consecutive days by 10 g/day. As control swine, skim milk powder to which Mn-lactoferrin was not added was fed to 4 young swine.

Symptom of diarrhea on the swine was observed for 3 days. The results are shown in Table 15.

TABLE 15

EFFECT OF Mn-LACTOFERRIN ON DIARRHEA OF YOUNG SWINE

| dose | curing rate (%) |
|---|---|
| control (skim milk powder) | 0/4 (0%) |
| composition (Mn-lf) | 5/6 (83.3%) |

From Table 14, it will be understood that viable counts of harmful bacteria in the intestine were reduced, and that those of useful bifidobacteria were increased by dosage of the composition containing Mn-lactoferrin.

It will be also understood from Table 15 that diarrhea in swine cured by dosage of the composition containing Mn-lactoferrin.

EXAMPLE 9

To a mixture of 490 g of sodium acetate unhydrated and 490 g of sodium chloride, 20 g of Mn-lactoferrin prepared in the same manner as in step (1–5) of Test 1 was added to thereby obtain 1000 g of an easily fluidal powdery composition.

To 4950 g of city water, 50 g of the resultant powdery composition was dissolved (concentration of the components; Mn-lf: 200 ppm; sodium acetate unhydrated: 0.49%; sodium chloride: 0.49%). In the resultant solution, 1 kg of sliced cabbage in the market was dipped for 10 minutes, then dipped out and packed and sealed in a plurality of containers (test samples). The resultant packages were kept at 10° C. for 1 week for observation. Control samples were prepared in the same manner as in the test samples, except that Mn-lactoferrin was not included in the solution.

The appearance and flavours of the treated sliced cabbage were observed for 1 week. The results are shown in Table 16.

TABLE 16

EFFECT OF Mn-LF ON PRESERVABILITY OF SLICED CABBAGE

| storage period (day) | appearance and taste of sliced cabbage | |
|---|---|---|
| | control | test sample |
| 0 | good in appearance and taste | good in appearance and taste |
| 3 | slightly drooped, good taste | good in appearance and taste |
| 5 | browny appearance, putrid smell | slightly drooped, good taste |
| 7 | — | browny appearance, putrid smell |

From Table 16, it will be understood that preservability of sliced cabbage is improved by the treatment with aqueous solution of the composition containing Mn-lactoferrin.

To 490 g of city water, 10 g of the same composition was dissolved (concentration of the components; Mn-lf: 400 ppm; sodium acetate unhydrated: 0.98%; sodium chloride: 0.98%).

With the resulting solution, the breasts of a Holstein cow (of 3 years age) having mammitis were thoroughly washed or rinsed before and after milking in the morning and in the afternoon for 3 consecutive days. Mammitis was completely cured after 3 days. From the microbial inspection, mammitis was caused by S. pyogenes.

EXAMPLE 10

To 10 kg of raw milk, 1 g of Zn-lactoferrin prepared in the same manner as in step (1–3) of Test 1, 0.5 g of Cu-lactoferrin prepared in the same manner as in step (1–4) of Test 1 and 0.50 g of Mn-lactoferrin prepared in the same manner in step (1–5) of Test 1 were dissolved (concentration of Zn-lf: 100 ppm; Cu-lf: 50 ppm; Mn-lf: 50 ppm). The resultant milk was aseptically distributed into a plurality of bottles and sealed to make test samples. Control samples were prepared in the same manner as in the test samples, except that Zn-, Cu and Mn-lf were not added to the raw milk.

The test and control samples were preserved at 10° C. for 8 days to observe the change of viable baterial count and flavour. The results are shown in Table 17.

TABLE 17

EFFECTS OF MIXTURE OF Zn—, Cu— AND Mn-LF ON PRESERVABILITY OF RAW MILK

| storage period (day) | control sample bacterial count | flavour | test sample bacterial count | flavour |
|---|---|---|---|---|
| 0 | $24 \times 10^4$ | good | $24 \times 10^4$ | good |
| 2 | $81 \times 10^4$ | good | $34 \times 10^4$ | good |
| 4 | $82 \times 10^5$ | slightly sour | $55 \times 10^4$ | good |
| 6 | $77 \times 10^6$ | putrid | $12 \times 10^5$ | good |
| 8 | $18 \times 10^8$ | putrid | $75 \times 10^5$ | slightly sour |

From Table 17, it will be apparent that addition of bioactive agent consisting of a mixture of Zn-, Cu- and Mn-lactoferrin improves preservability of raw milk.

EXAMPLE 11

To 800 g of skim milk powder, 100 g of Zn-lactoferrin prepared in the same manner in step (1–3) of Test 1, 50 g of Cu-lactoferrin prepared in the same manner as in step (1–4) of Test 1 and 50 g of Mn-lactoferrin prepared in the same manner in step (1–5) of Test 1 were respectively added to thereby obtain 1000 g of an easily fluidal composition having biological activities.

To 5 healthy Holstein cows of 1-2 years age, the resultant composition was fed twice a day for 2 days by 30 g at a time together with ordinary feed in the morning and in the afternoon.

Viable bacterial counts in the feces before and after ingestion of Zn-, Cu- and Mn-lactoferrin were compared. The results are shown in Table 18.

TABLE 18

EFFECT OF DOSAGE OF Zn—, Cu— AND Mn-LACTOFERRIN ON VIABLE BACTERIAL COUNTS IN FECES

| cow No. | E. coli before | E. coli after | C. perfringes before | C. perfringes after | Bifidobacterium before | Bifidobacterium after |
|---|---|---|---|---|---|---|
| 1 | $7.6 \times 10^7$ | $1.1 \times 10^7$ | $4.1 \times 10^7$ | $1.9 \times 10^6$ | $7.1 \times 10^7$ | $6.5 \times 10^8$ |
| 2 | $6.6 \times 10^8$ | $1.4 \times 10^7$ | $5.0 \times 10^7$ | $1.0 \times 10^7$ | $5.4 \times 10^7$ | $5.9 \times 10^8$ |
| 3 | $3.2 \times 10^8$ | $5.2 \times 10^7$ | $3.7 \times 10^7$ | $7.7 \times 10^6$ | $7.8 \times 10^7$ | $9.9 \times 10^8$ |
| 4 | $8.0 \times 10^7$ | $2.1 \times 10^7$ | $7.8 \times 10^6$ | $1.2 \times 10^6$ | $2.1 \times 10^7$ | $6.7 \times 10^8$ |
| 5 | $6.5 \times 10^8$ | $1.0 \times 10^8$ | $8.5 \times 10^6$ | $6.0 \times 10^5$ | $3.9 \times 10^7$ | $5.2 \times 10^8$ |

The same composition was fed to 6 young swine having diarrhea for 3 days by 10 g/day. As control swine, skim milk powder to which the mixture of Zn-, Cu- and Mn-lactoferrin was not added was fed to 4 young swine.

Symptom of diarrhea on the swine was observed for 3 days. The results are shown in Table 19.

TABLE 19

EFFECT OF A MIXTURE OF Zn—, Cu— AND Mn-LACTOFERRIN ON DIARRHEA OF YOUNG SWINE

| dose | curing rate (%) |
|---|---|
| control (skim milk powder) | 0/4 (0%) |
| composition (Zn—, Cu— AND Mn-lf) | 5/6 (83.3%) |

From Table 18, it will be understood that viable counts of harmful bacteria in the intestine were reduced, and that those of useful Bifidobacteria were remarkably increased by dosage of the mixture of Zn-, Cu- and Mn-lactoferrin.

It will be also understood from Table 19 that diarrhea on swine can be cured by dosage of the mixture of Zn-, Cu- and Mn-lactoferrin.

From the foregoing tests and examples, it will be understood that the bioactive agents consisting of one or more lactoferrin-compounds and the compositions comprising the bioactive agents in accordance with the present invention can be utilized in various purposes in various aspects.

Although only a limited number of tests and examples have been described in this specification, it should be noted that the present invention should not be limited thereto, but various modifications and alterations can be made within the concept of the present invention.

It will be understood that the present invention provides not only the bioactive agents but also the compositions, materials and products containing the bioactive agent as the effective component thereof to afford the biological activities thereto, that is, growth-inhibitory activity against certain harmful microorganisms and growth-promoting activity upon certain useful microorganisms.

It will be also understood that the present invention provides a method for treating those materials which are edible to human beings and animals or which are applicable to a portion of animals body with the bioactive agents or the composition containing the bioactive agents for affording the biologial activities thereto or for prolonging the shelf-life thereof.

EFFECTS OF THE INVENTION

The effects of the present invention are as follows:

(1) The bioactive agents as well as the compositions, materials and products containing the bioactive agent in accordance with the present invention may inhibit proliferation of harmful microorganisms and may promote proliferation of useful microorganisms both in vitro and in vivo.

(2) The bioactive agents as well as the compositions, materials and products containing the bioactive agents in accordance with the present invention are effective for therapy against infectious diseases as well as prevention therefrom on human beings and other animals.

(3) The bioactive agents as well as the compositions, materials and products containing the bioactive agent in accordance with the present invention are effective to improve defensive abilities of human beings and other animals against infectious diseases.

(4) The bioactive agents as well as the compositions containing the bioactive agents in accordance with the present invention are effective to improve preservability of foods and feeds when they are added or treated therewith.

(5) The materials and the products containing the bioactive agents in accordance with the present invention may have prolonged shelf-life.

What is claimed is:

1. A method of promoting proliferation of a useful microorganism selected from the group consisting of *Bifidobacterium bifidum*, *Bifidobacterium infantis*, *Bifidobacterium breve*, *Bifidobacterium longum*, *Bifidobacterium pseudolongum*, *Bifidobacterium animalis*, *Lactobacillus acidophilus* and *Lactobacillus casei*, comprising adding a bovine lactoferrin substance selected from the group consisting of Zn-lactoferrin, Cu-lactoferrin and Mn-lactoferrin to a food containing said microorganism, such that said bovine lactoferrin substance is present in said food in a concentration not less than 100 ppm.

2. A method of suppressing proliferation of a harmful microorganism selected from the group consisting of *Escherichia coli, Staphylococcus aureus, Bacillus subtilis, Pseudomonas fluorescens, Clostridium perfringens* and *Streptococcus pyogenes*, comprising applying an aqueous solution of a bovine lactoferrin substance selected from the group consisting of Zn-lactoferrin, Cu-lactoferrin and Mn-lactoferrin to a surface contaminated with said microorganism, such that said bovine lactoferrin substance is present in said solution in a concentration not less than 100 ppm.

3. A method of promoting proliferation of a useful microorganism selected from the group consisting of *Bifidobacterium bifidum, Bifidobacterium infantis, Bifidobacterium breve, Bifidobacterium longum, Bifidobacterium pseudolongum, Bifidobacterium animalis, Lactobacillus acidophilus* and *Lactobacillus casei*, comprising administering to an animal a composition comprising an animal feed and a bovine lactoferrin substance selected from the group consisting of Zn-lactoferrin, Cu-lactoferrin and Mn-lactoferrin, such that said bovine lactoferrin substance is present in said animal feed in a concentration not less than 100 ppm.

4. A method of suppressing proliferation of a harmful microorganism selected from the group consisting of *Escherichia coli, Staphylococcus aureus, Bacillus subtilis, Pseudomonas fluorescens, Clostridium perfringens* and *Streptococcus pyogenes*, comprising administering a composition comprising an animal feed and a bovine lactoferrin substance selected from the group consisting of Zn-lactoferrin, Cu-lactoferrin and Mn-lactoferrin, said bovine lactoferrin substance being present in said animal feed in a concentration not less than 100 ppm, to an animal in need thereof.

5. A method of suppressing proliferation of a harmful microorganism in a food, said harmful microorganism being selected from the group consisting of *Escherichia coli, Staphylococcus aureus, Bacillus subtilis, Pseudomonas fluorescens, Clostridium perfringens* and *Streptococcus pyogenes*, comprising adding a bovine lactoferrin substance selected from the group consisting of Zn-lactoferrin, Cu-lactoferrin and Mn-lactoferrin to said food, said bovine lactoferrin substance being present in said food in a concentration not less than 100 ppm.

6. The method of claim 1, wherein said bovine lactoferrin substance is present in a concentration of from 100 ppm to 25% by weight of said food.

7. The method of claim 6, wherein said bovine lactoferrin substance is present in a concentration of from 250 ppm to 25% by weight of said food.

8. The method of claim 2, wherein said bovine lactoferrin substance is present in a concentration of from 100 ppm to 1000 ppm by weight of said solution.

9. The method of claim 3, wherein said bovine lactoferrin substance is present in a concentration of from 100 ppm to 25% by weight of said animal feed.

10. The method of claim 9, wherein said bovine lactoferrin substance is present in a concentration of from 250 ppm to 25% by weight of said animal feed.

11. The method of claim 4, wherein said bovine lactoferrin substance is present in a concentration of from 100 ppm to 25% by weight of said animal feed.

12. The method of claim 5, wherein said bovine lactoferrin substance is present in a concentration of from 100 ppm to 25% by weight of said food.

13. The method of claim 12, wherein said bovine lactoferrin substance is present in a concentration of from 250 ppm to 25by weight of said food.

14. The method of claim 1, wherein said food is milk.

15. The method of claim 1, wherein said food is a fermentation product.

16. The method of claim 4, wherein said bovine lactoferrin substance is administered orally to an animal or human being in need of prevention from or treatment of diarrhea.

17. The method of claim 2, wherein said bovine lactoferrin substance is administered percutaneously to an animal or human being in need of prevention from or treatment of a microbial infection of skin.

18. The method of claim 2, wherein said bovine lactoferrin substance is administered percutaneously to an animal in need of prevention from or treatment of mammitis.

* * * * *